United States Patent [19]

Kappas et al.

[11] Patent Number: 4,684,637

[45] Date of Patent: Aug. 4, 1987

[54] METHOD OF DECREASING RATE OF HEME METABOLISM

[75] Inventors: Attallah Kappas, Rye; George Drummond, New York, both of N.Y.; 42

[73] Assignee: The Rockefeller University, New York, N.Y.

[21] Appl. No.: 768,163

[22] Filed: Aug. 19, 1985

Related U.S. Application Data

[63] Continuation of Ser. No. 397,230, Jul. 12, 1982, abandoned, and a continuation-in-part of Ser. No. 285,373, Jul. 15, 1981, abandoned.

[51] Int. Cl.$^4$ ............................................ A61K 31/555
[52] U.S. Cl. .................................... 514/185; 514/493; 514/505

[58] Field of Search ........................ 514/493, 505, 185

[56] References Cited

PUBLICATIONS

Maines et al.—Science, vol. 198 (Dec. 23, 1977), pp. 1215–1221.
Maines—Biochemica Biophysica Acta, vol. 673 (1981).
Fiechtner et al.—Chem. Abst., vol. 92 (1980), p. 106,051g.

Primary Examiner—Sam Rosen
Attorney, Agent, or Firm—Wyatt, Gerber, Shoup, Scobey and Badie

[57] ABSTRACT

Methods for decreasing the rate of metabolism of heme in mammals by administration of tin or chromium protoporphrins IX, and compositions useful therefore.

32 Claims, No Drawings

METHOD OF DECREASING RATE OF HEME METABOLISM

This invention was made in the course of a grant from the National Institutes of Health.

RELATED APPLICATION

This application is a continuation in part of previously filed, concurrent patent application Ser. No. 285,373, filed July 15, 1981, and a continuation of Ser. No. 397,230, filed July 12, 1982, both now abandoned.

BACKGROUND OF THE INVENTION

This invention relates to methods and compositions useful for decreasing the rate of metabolism of heme in mammals. More specifically, it relates to the use of metal protoporphyrins IX to decrease the rate at which heme is metabolized in living mammals.

Iron protoporphyrin, also called heme, or more accurately ferroprotoporphyrin IX, is the specific porphyrin isomer found in mammalian whole blood. It is an essential component in the respiratory chain and in the energy transfer reactions which take place in the mammalian body. It is synthesized and degraded by known metabolic routes involving known enzymatic reactions.

In the normal course of degradation, heme first undergoes a ring opening reaction to form biliverdin which then converts to bilirubin. Bilirubin is toxic, but normally this toxicity is not manifested since it rapidly combines with albumin and is transported to the liver. In the liver, the protein is released and the bilirubin is converted to the corresponding diglucuronide by reaction with uridine diphosphoglucuronate. The diglucuronide is soluble and excreted.

A number of synthetic analogs of iron protoporphyrin IX are known. They are commercially available or are readily synthesized by known methods. These include, for example, platinum, zinc, nickel, cobalt, copper, silver, manganese, chromium and tin protoporphyrin IX. For convenience herein, these compounds are referred to generically as Me-protoporphyrin, where Me stands for metal, and specifically by utilizing the chemical symbol for the metal such as Cr-protophorphyrin and Sn-protophorphyrin for the chromium and tin compounds respectively.

One of the more difficult aspects of the toxicity of bilirubin is the so-called jaundice of the newborn which arises from an undesirably high concentration of bilirubin in the blood of newborn mammals. In the period immediately after birth, there is a high concentration of heme in mammalian blood. There is also a high degree of heme oxygenase activity. This enzyme is essential to the metabolism of heme to bilirubin. The combination of factors leads to rapid metabolism of large amounts of heme and results in high concentrations of bilirubin in the body fluids of neonates. Since bilirubin is yellow, the infant appears yellow. Hence, the name jaundice of the newborn.

Free bilirubin is fat soluble and readily crosses the blood-brain barrier causing extensive and serious brain damage. One manifestation of the toxicity of bilirubin is kernicterus or bilirubin encephalopathy. It may present clinically as lethargy, rigidity, opisthotonus, high-pitched cry, fever and convulsions. It may result in death. Survivors often have cerebral palsy, frequently of the choreoathetoid type, deafness, mental retardation and other neurologic defects in infancy or early childhood.

The principal treatments for hyperbilirubinemia have been phototherapy and exchange transfusions. In the former treatment, the patient is exposed to increased intensities of light in the visible range particularly between 420 and 470 nm. This results in increased oxidation of bilirubin or conversion by other mechanisms to products that are not yet fully identified. The treatment is widespread, particularly in the United States, but is not regarded as fully satisfactory since there are many as yet unanswered questions concerning its safety and effectiveness.

The more traumatic procedure of exchange transfusion is indicated with full term infants when there is an unconjugated bilirubin level of 20 mg/dl. With premature infants, the transfusion may be considered necessary at concentrations as low as 9 mg/dl. It is now generally accepted that concentrations which do not exceed 2.0 mg/dl can be tolerated without unnecessary damage to the infant. However, it appears clearly to be desirable to keep the level of this highly toxic chemical lower than 2 mg/dl if possible.

Increased concentrations of bilirubin often appear in the blood of adult humans and other mammals with sickle cell anemia, thalassemia and other congenital anemias as well as with animals and humans with acquired liver diseases. With such individuals, the concentration of bilirubin rarely reaches the high levels observed with neonates. It does, however, reach levels which may be toxic and should be controlled.

It is desirable, therefore, to have available methods and materials for inhibiting the metabolism of heme so as to decrease the rate at which it degrades and the rate at which bilirubin accumulates in the blood.

THE INVENTION

It has now been discovered that the rate at which heme metabolizes can be decreased in mammals by administration of an effective amount of a synthetic Me-protoporphyrin. The presently preferred compounds are Sn-protoporphyrin and Cr-protoporphyrin. Both of these compounds are readily synthesized in pure form at reasonable costs and are therefore readily available. They are water soluble and may be compounded with a variety of pharmaceutically acceptable carriers. The tin compound appears to be the more active.

To determine the efficacy of Sn-protoporphyrin for controlling the rate of heme metabolism, neonatal rats were injected subcutaneously at birth, and at 12, 24, 48 and 72 hours postnatally with 0.1 ml solutions of Sn-protoporphyrin. To prepare the solutions for parenteral injection, the material was taken up in a small volume of 0.2N sodium hydroxide, adjusted to pH 7.4 with one normal hydrochloric acid and made up to final volume with 0.9% sodium chloride. The compositions as prepared and used contained sufficient Sn-protoporphyrin to provide about 100 $\mu$mol/Kg body weight in each 0.1 ml injection. Control neonates received an equivalent volume of saline at each time point. Groups of neonates (6–30 animals per group) were sacrificed at selected time intervals.

The treated animals and the controls were assayed for heme oxygenase activity and bilirubin concentration. Since heme oxygenase is an essential component in the catabolism of heme, an increase in heme oxygenase activity is indicative of an increase in the rate of heme catabolism. Heme oxygenase was assyed as described by Maines and Kappas in J. Biol. Chem., 253, 2321-2326 (1978). Total bilirubin in serum was estimated by the method of Roth, Clin. Chem. Acta., 17, 487-492 (1967).

In a six week study, it was found that, with controls, hepatic heme oxygenase levels in neonates rose rapidly, reaching levels four fold above those characteristic of adult liver before gradually declining to normal adult levels between days 21 and 42. In the Sn-protoporphyrin treated neonates, the administration of the active agent completely prevented the normal marked increase in hepatic heme oxygenase activity after birth. Indeed, in these neonates, the heme oxygenase activity declined immediately (1 day) to levels less than half the levels of the controls. They remained well below the control levels for about three weeks, and then rose gradually to finally attain the normal control levels at about day 42.

Sn-protoporphyrin administration resulted in an immediate and significant lowering of serum bilirubin levels in treated animals. This low level of bilirubin concentration continued until about the fourth day and then remained substantially the same as the controls throughout the balance of the 42 day study period.

Similar studies were conducted with neonatal rats treated subcutaneously with 2 and 10 micromoles per kilogram of Cr-protoporphyrin soon after birth. Various organs were analyzed for heme oxygenase activity and bilirubin concentration. The results were compared with controls each of which were treated subcutaneously with 0.1 ml of saline.

The results for heme oxygenase activity in liver, kidney and spleen in nanamoles heme oxygenase per milligram microsomal protein per hour are shown below.

TABLE 1

|  | Time (days) | | | | | | | | |
|---|---|---|---|---|---|---|---|---|---|
|  | 1 | 2 | 3 | 5 | 7 | 10 | 14 | 21 | 35 |
| Liver | | | | | | | | | |
| Control | 6.01 | 7.78 | 8.96 | 10.13 | 6.87 | 6.38 | 4.33 | 2.64 | 2.60 |
| 2 μmol/Kg | — | 5.81 | 5.60 | 5.36 | 4.42 | 3.62 | 2.24 | 1.94 | 2.38 |
| 10 μmol/Kg | — | 1.67 | 1.43 | 1.22 | 0.85 | 0.85 | 0.78 | 0.56 | 1.23 |
| Kidney | | | | | | | | | |
| Control | 2.59 | 2.14 | 2.13 | 1.28 | 2.64 | 2.84 | 1.31 | 1.05 | 0.94 |
| 2 μmol/Kg | — | 0.36 | 0.72 | 0.94 | 1.17 | 1.67 | 0.74 | 0.61 | 0.58 |
| 10 μmol/Kg | — | 0 | 0.42 | 0.59 | 0.48 | 0.34 | 0.41 | 0.16 | 0.45 |
| Spleen | | | | | | | | | |
| Control | 6.25 | 8.19 | 15.05 | 16.20 | 13.03 | 15.05 | 16.76 | 9.12 | 9.63 |
| 2 μmol/Kg | — | 7.33 | 11.13 | 15.13 | 11.18 | 13.87 | 16.62 | 10.28 | 15.55 |
| 10 μmol/Kg | — | 3.97 | 4.62 | 2.76 | 6.19 | 9.53 | 10.34 | 8.06 | 13.72 |

It is clear from the above that the effect of the administration of Cr-protoporphyrin is to cause an immediate decrease in heme oxygenase. Similar results were observed with serum bilirubin as shown in the following Table 2 in which the concentration is expressed in milligrams per deciliter.

TABLE 2

| Serum Bilirubin | 1 | 2 | 3 | 5 | 7 | 10 | 14 |
|---|---|---|---|---|---|---|---|
| Control | 0.39 | 0.48 | 0.42 | 0.31 | 0.33 | 0.46 | 0.38 |
| 2 μmol/Kg | — | 0.39 | 0.33 | 0.28 | 0.32 | 0.33 | 0.40 |
| 10 μmol/Kg | — | 0.43 | 0.33 | 0.24 | 0.30 | 0.33 | 0.28 |

Studies were carried out with adult rats treated with Sn-protoporphyrin to determine the effect on heme oxygenase activity and bilirubin production. Three rats weighing about 230 grams each were injected subcutaneously with 50 μmol/Kg of Sn-protoporphyrin in isotonic saline at pH 8. Three controls were similiary treated with isotonic saline. The rats were sacrificed sixteen hours after treatment. The microsomal protein of the separate livers and of the three combined kidneys was estimated and heme oxygenase activity determined according to the method of Maines and Kappas. This procedure measures the heme oxygenase activity by determining the amount of bilirubin produced. The results are shown in Table 3. The concentration unit for bilirubin is nanamoles bilirubin formed per milligram protein per hour.

TABLE 3

|  | LIVER | KIDNEY (COMBINED) |
|---|---|---|
| Control 1 | 2.19 | |
| Control 2 | 3.29 | 1.24 |
| Control 3 | 2.39 | |
| Experiment 1 | 0.95 | |
| Experiment 2 | 0.95 | 0.055 |
| Experiment 3 | 1.53 | |

It is readily apparent from the above that Sn-protoporphyrin is extremely effective for reducing bilirubin production and heme oxygenase activity in adult mammals.

With neonate mammals, the therapeutic compositions of this invention will be administered promptly after birth at a dosage of from 10 to 25 μmol/Kg of body weight in animals and 0.1 to 2.5 μmol/Kg of body weight in humans. While any of the usual parenteral routes may be employed, intramuscular or intravenous injection is preferred. Normally, one injection will suffice to maintain the bilirubin concentration at a desired low level until the neonate reaches the age where the metabolism of heme is in balance. It is preferred,, however, to monitor the serum bilirubin concentration and to utilize a booster dose, if necessary. The physician or veterinarian will select the appropriate dosage. It will normally be within the above range, but may be varied to deal with specific conditions.

With adults afflicted with sickle cell anemia or another condition resulting in increased bilirubin concentration, the dosage unit is normally smaller, since in all but the most acute situations, the bilirubin concentration is not as high as in neonates. The standard dosage with adults will normally be from about 0.05 to 1 μmol/Kg of body weight.

In order to have appropriate dosage units available, the compositions of this invention will normally be prepared in bulk at concentrations of from 100 to 2500 μmol/liter of buffered isotonic aqueous solution at pH 7 to 8 and subdivided into dosage units containing approximately 0.1 to 2.5 μmol/ml of solution.

The usual pharmaceutical carriers are isotonic aqueous salt or glucose solutions buffered to a pH of about 7 to 8, normally 7.4

Therapeutic compositioos can also be provided in lyophilized powder form to be reconstituted with water to the clinical dosage. For example, the selected Me-protoporphyrin can be taken up in 0.1 molar phosphate or other pharmaceutically acceptable buffer containing sufficient saline or other solute to form isotonic solutions, and freeze dried to form a powder. The powder can be reconstituted with distilled water or saline solution to provide solutions containing 0.1 to 2.5 μmol/ml of Me-protoporphyrin per milliliter of solution.

What is claimed is:

1. A method of decreasing the rate of metabolism of heme in mammals in need of such treatment by administering to the mammal an amount of Sn-protoporphyrin or Cr-protoporphyrin which is effective to decrease said rate.

2. A method as in claim 1 wherein Sn-protoporphyrin is administered.

3. A method as in claim 1 wherein Cr-protoporphyrin is administered.

4. A method as in claim 2 wherein the mammal is a human.

5. A method as in claim 3 wherein the mammal is a human.

6. A method of decreasing the rate of bilirubin accumulation in neonatal mammals which comprises administering to the neonate promptly after birth an amount of Sn-protoporphyrin or Cr-protoporphyrin which is effective to decrease said rate.

7. A method as in claim 6 wherein Sn-protoporphyrin is administered.

8. A method as in claim 6 wherein Cr-protoporphyrin is administered.

9. A method as in claim 7 wherein the neonate is human.

10. A method as in claim 8 wherein the neonate is human.

11. A pharmaceutical composition containing 100 to 2500 μmol of Sn-protoporphyrin or Cr-protoporphyrin per liter of non-toxic, parenteral buffered isotonic aqueous solution at pH 7 to 8.

12. A composition of claim 11 containing Sn-protoporphyrin.

13. A composition of claim 11 containing Cr-protoporphyrin.

14. A pharmaceutical composition in dosage unit form containing 0.1 to 2.5 μmol of Sn-protoporphryin or Cr-protoporphyrin per milliliter of non-toxic, parenteral buffered isotonic aqueous solution at pH 7 to 8.

15. A composition of claim 14 containing Sn-protoporphyrin.

16. A composition of claim 14 containing Cr-protoporphyrin.

17. A non-toxic, parenteral pharmaceutical composition useful for decreasing the rate of metabolism of heme in mammals in need of such decreased rate comprising Sn-protporphyrin or Cr-protoporphyrin together with a pharmaceutically acceptable carrier.

18. A composition of claim 17 containing Sn-protoporphyrin.

19. A composition of claim 17 containing Cr-protoporphyrin.

20. A non-toxic, parenteral pharmaceutical composition useful for decreasing the rate of metabolism of heme in mammals in need of such decreased rate comprising a buffered isotonic aqueous solution containing an amount of Sn-protoporphyrin or Cr-protoporphyrin which is effective to decrease said rate.

21. A composition of claim 20 containing Sn-protoporphyrin.

22. A composition of claim 20 containing Cr-protoporphyrin.

23. A non-toxic, parenteral pharmaceutical composition useful for decreasing the rate of metabolism of heme in mammals in need of such decreased rate comprising a buffered isotonic aqueous saline solution containing an amount of Sn-protoporphyrin or Cr-protoporphyrin which is effective to decrease said rate.

24. A composition of claim 23 containing Sn-protoporphyrin.

25. A composition of claim 23 containing Cr-protoporphyrin.

26. A non-toxic, parenteral pharmaceutical composition useful for decreasing the rate of metabolism of heme in mammals in need of such decreased rate comprising a buffered isotonic aqueous glucose solution containing an amount of Sn-protoporphyrin or Cr-protoporphyrin which is effective to decrease said rate.

27. A composition of claim 26 containing Sn-protoporphyrin.

28. A composition of claim 26 containing Cr-protoporphyrin.

29. A pharmaceutical composition of claims 17, 18, 19, 20, 21, 22, 23, 24, 25, 26, 27 or 28 in dosage unit form.

30. A lyophilized composition of claim 17.

31. A lyophilized composition of claim 18.

32. A lyophilized composition of claim 19.

* * * * *